United States Patent [19]

Deihl

[11] Patent Number: 4,525,341

[45] Date of Patent: Jun. 25, 1985

[54] METHOD OF ADMINISTERING VITAMINS

[75] Inventor: Joseph A. Deihl, Phoenix, Ariz.

[73] Assignee: Mayor Pharmaceutical Laboratories, Inc., Tempe, Ariz.

[21] Appl. No.: 598,480

[22] Filed: Apr. 9, 1984

[51] Int. Cl.³ .................. A61K 9/00; A61K 31/59; A61K 31/365; A61K 31/07

[52] U.S. Cl. .................. 424/43; 424/195.1; 514/52; 514/251; 514/356; 514/458; 514/474; 514/560; 514/563; 514/681; 514/725; 514/904

[58] Field of Search .................. 424/45, 43, 195, 236, 424/237, 252, 255, 266, 273 R, 280, 284, 331, 344

[56] References Cited

U.S. PATENT DOCUMENTS

| | | | |
|---|---|---|---|
| 3,282,781 | 11/1966 | Macek et al. | 424/45 |
| 3,584,115 | 6/1971 | Gebhart et al. | 424/45 |
| 3,957,966 | 5/1976 | Valan | 424/45 |

OTHER PUBLICATIONS

Chem. Abst. 73:59219(p) (1970)–Valfre.
Chem. Abst. 99; 86922(f)(1983)–Jipucomu.

*Primary Examiner*—Douglas W. Robinson
*Attorney, Agent, or Firm*—William H. Drummond

[57] ABSTRACT

A method for administering vitamins to an air-breathing animal consists of introducing the vitaminic aerosol containing a breath freshener into the nose or mouth opening of the animal.

1 Claim, No Drawings

METHOD OF ADMINISTERING VITAMINS

The invention pertains to a method for administering vitamins to a pulmonifer.

In a more particular aspect, the invention relates to a method of administering a sprayable vitaminic composition which may include other ingredients such as breath fresheners, flavoring agents and the like.

In still another, further and more particular aspect, the invention pertains to convenient methods for administering vitamins to humans, in which inconvenience or complications are reduced in comparison to conventional methods such as oral ingestion of tablets along with water or other drinking fluids or by parenteral injections.

Vitamins are complex organic substances found variously in most foods and are essential, in small amounts, for the normal functioning of most living organisms. For example, vitamins are a critically necessary component of the diet of most higher animals, including humans. When the normal diet fails to furnish minimum quantities of essential vitamins, it is common practice to supplement the diet by artificially inducing the required amounts into the body. Common methods of introduction include oral ingestion of tablets or liquid solutions containing the vitamins (which may require concurrent ingestion of a suitable carrier liquid such as water or other drinkable liquid to aid in swallowing the vitamin composition and washing it into the gastro-intestinal system of the human). Similarly, but less frequently, vitamins are introduced by parenteral injection.

Parenteral injection and, to a lesser extent, oral ingestion may be painful, disagreeable or, at the very least, inconvenient. Particular problems are encountered in administration of vitamins by involuntary techniques such as forced introduction into the oral cavity and forced swallowing which may be accompanied by gagging or vomiting. Parenteral injection may induce involuntary muscle spasms or contractions which may be injurious to the body or may even induce voluntary retaliatory reaction, such as biting, striking, kicking, etc.

Of more conventional concern, particularly in the case of voluntarily introducing vitamins into human bodies, matters of inconvenience such as difficulty of swallowing, the temporary unavailability of accompanying drinkable liquids or simple embarrassment may inhibit the subject from taking recommended vitamin supplements.

Finally, mere forgetfulness may also induce failure to voluntarily ingest appropriate quantities of supplemental vitamins.

Accordingly, it would be highly advantageous to provide more convenient compositions and methods for introducing supplemental vitamins into the human body. It would be especially advantageous to provide such compositions and methods which are particularly suited to overcome natural reluctance of humans to voluntarily ingest or parenterally receive vitamin compositions. Likewise, it would be highly advantageous to provide methods and compositions which can be conveniently employed to introduce vitamins into the human body by techniques which overcome forgetfulness, embarrassment or temporary lack of suitable concommitants.

I have now discovered novel vitaminic compositions in the form of an aerosol comprising a suspension of droplets containing at least one vitamin dispersed in a carrier gas.

According to the preferred embodiments of the invention which are especially useful in connection with introducing supplemental vitamins into humans, the compositions also include breath fresheners and/or flavoring agents.

The method of the invention comprises the step of introducing the aerosol composition into one of the pulmonary openings of the pulmonifer, i.e., the nose or mouth. This technique is especially suited to involuntarily introduce vitamins into the human body as there is no necessity for further action on the part of the administering clinician such as, e.g., inducing involuntary swallowing. The vitamin compositions can be simply sprayed into the nose or mouth the vitamins find the way into the proper body processes by absorption through the mucous membranes and/or simple swallowing according to normal salivary mechanisms.

As used herein, the term "aerosol" includes both true coloidal suspensions of liquid droplets in the gaseous carrier as well as simple temporary suspensions of such droplets in the carrier.

Obviously, the carrier must be non-toxic to the pulmonifer.

Typical carriers may advantageously include air and non-toxic propellant gases such as are commonly employed in food products dispensed as foams, e.g., carbon dioxide, nitrogen and the like, or non-toxic halocarbons such as disclosed in U.S. Pat. No. 3,490,923.

The vitamins which can be employed in the practice of the invention include all of the known complex organic substances which have been identified as having the requisite biological activity and, for example, may include:

vitamin A, a fat-soluble aliphatic alcohol, $C_{20}H_{29}OH$, found in fish-liver oil, egg yolk, butter, etc., and (as carotene) in carrots and other vegetables: a deficiency of this vitamin results in night blindness and degeneration of epithelial tissue: it occurs in two forms, vitamin $A_1$ and vitamin $A_2$.

vitamin B (complex), a group of unrelated water-soluble substances including: (a) vitamin $B_1$ (thiamine); (b) vitamin $B_2$ (riboflavin); (c) vitamin $B_6$ (pyridoxine); (d) nicotinic acid; (e) pantothenic acid; (f) biotin (also called vitamin H); (g) inositol; (h) para-aminobenzoic acid; (i) choline; and (j) folic acid.

vitamin C, an organic compound, $C_6H_3O_6$, occurring in citrus fruits, tomatoes and various vegetables: a deficiency of this vitamin tends to produce scurvy: also called ascorbic acid, cevitamic acid.

vitamin D, any of several related vitamins occurring in fish-liver oils, milk, egg yolks, etc.: a deficiency of this vitamin tends to produce rickets; specifically, (a) vitamin $D_1$, a mixture of calciferol with another sterol prepared by the ultraviolet irradiation of ergosterol; (b) vitamin $D_2$ (calciferol); (c) vitamin $D_3$, a substance similar to vitamin $D_2$, found chiefly in fish-liver oils.

vitamin E, a substance consisting of a mixture of tocopherols, believed to restore fertility to sterile mammals: formerly called vitamin X.

vitamin G, vitamin $B_2$ (riboflavin).

vitamin H, biotin.

vitamin K, a vitamin occuring in certain green vegetables, fish meal, hempseed, etc. and used to promote blood clotting, and thus prevent hemorrhage, by aiding in the synthesis of prothrombin by the liver:

the two varieties are vitamin $K_1$, found chiefly in alfalfa leaves, and vitamin $K_2$, found chiefly in fish meal.

vitamin P, a mixture of the flavones occurring especially in citrus juice and paprika: a deficiency of this vitamin results in the increased permeability of capillary walls and, hence, greater susceptibility to hemorrhage: also called citrin.

vitamin X, a former name for vitamin E.

The liquid carrier for the vitamin will be chosen with reference to the solubility and/or suspendibility of the vitamins and/or breath freshener and flavoring agent and, for example, may be a non-toxic alcohol, water or an aqueous alcohol. According to the presently preferred embodiments of the invention, the solvent system is 200 proof spirits. If the vitamin composition does not contain water-insoluble components, simple water solutions of the vitamins are preferred as the liquid component of the aerosol.

Breath fresheners which may be advantageously employed include naturally occurring deodorant or perfuming compounds such as mints, cinnamon, lemon, non-toxic flower oils, etc. Some of these components may also impart desirable tastes and are useful for the additional function of flavoring components.

Useful flavoring ingredients include typical mint, spearmint, wintergreen, cinnamon, vanilla, cherry, citrus and other fruit derivatives.

The aerosols of the present invention are produced by any suitable technique for reducing the liquid phase to a fine spray in a carrier gas, i.e., "atomizing" the liquid. Prior art atomizers are suitable including various spray dispensers for liquids such as are commonly employed in dispensing perfumes, deodorants, breath deodorants, nose and throat medicines, etc. These include so-called "pressurized" atomizer devices which contain a quantity of liquid and the propellant gas under pressure and which mix the components and dispense the aerosol by merely opening a finger-actuated valve. Alternatively, atomizers can be employed which store the liquid component at atmospheric pressure and which are equipped with a combination finger-actuated pump-atomizing valve which mixes the liquid with ambient air and dispenses the resulting air-liquid aerosol.

To administer the vitaminic aerosols described above, it is only necessary to spray appropriate quantities of the aerosol into the mouth or nose (pulmonary opening) of the of the subject. In the case of administration through the nasal passages, the liquid components of the aerosol upon separation drains into the esophagus and is swallowed in the conventional fashion. When introduced into the oral cavity, the liquid components mixes with the saliva and is swallowed normally. Certain vitamins may be partially introduced into the body by absorption through the mucous membrane.

It is only necessary to introduce minor effective amounts of the aerosol into the pulmonary openings, i.e., an amount sufficient to cause the introduction of a sufficient quantity of the vitamin carried into the body to cause a beneficial physiological effect. The introduction of the aerosol may be carried out semi-continuously as the recipient breathes and/or swallows normally or in separate administrations at spaced periods throughout the waking hours.

The following examples are presented as non-limiting illustrations depicting the presently preferred embodiments of the invention.

EXAMPLE 1

The following liquid composition is prepared by mixing the ingredients indicated into the alcohol carrier until they are dissolved and/or suspended in the carrier.

| Ingredient | Parts by Weight |
|---|---|
| Carrier alcohol (200 proof spirit) | 87.903 |
| Peppermint flavoring oil | 3.1 |
| Glycerine | 2.16 |
| Emulsifier (Tween-80) | 0.16 |
| Fructose (flavoring agent) | 2.08 |
| Ascorbic acid | 2.15 |
| Vitamin E | 1.08 |
| Niacinamide | 0.72 |
| Pentothenic acid | 0.34 |
| Vitamin A | 0.12 |
| Pyridoxine hydrochloride | 0.072 |
| Riboflavin | 0.061 |
| Thiamine hydrochloride | 0.054 |
| Cyanocobalanine | 0.000093 |

EXAMPLE 2

The vitaminic composition of Example 1 is used to produce an aerosol by loading the liquid composition into a finger plunger pump-actuated throat spray atomizer. Depression of the finger pump produces a fine mist which is conveniently directly into the mouth. The peppermint oil produces a pleasant flavoring sensation in the mouth and also functions as a breath odor mask. The fructose contributes to the pleasant taste of the composition. The glycerine modifies the viscosity of the composition to provide better spraying characteristics. The emulsifier maintains certain of the partially insoluble components in suspension until the aerosol is produced.

Having described my invention in such terms as to enable those skilled in the art to understand and practice it and having identified the presently preferred embodiments thereof, I claim:

1. A method for autogenously administering vitamins to a human subject concurrently with the use of an aerosol breath spray, comprising the steps of:

(a) forming a sprayable liquid composition comprising
  (i) a breath freshening agent,
  (ii) at least one vitamin in a diet supplemental amount selected from the class consisting of vitamins A, B, C, D, E, G, H, K and P, and
  (iii) a non-toxic liquid carrier for said breath freshening agent and said vitamin; and (b) spraying an effective amount of an aerosol of said composition into the mouth of said subject.

* * * * *

(12) EX PARTE REEXAMINATION CERTIFICATE (5385th)
United States Patent
Deihl

(10) Number: US 4,525,341 C1
(45) Certificate Issued: Jun. 6, 2006

(54) METHOD OF ADMINISTERING VITAMINS

(75) Inventor: Joseph A. Deihl, Phoenix, AZ (US)

(73) Assignee: Mayor Pharmaceutical Laboratories, Inc.

Reexamination Request:
No. 90/005,411, Jul. 2, 1999

Reexamination Certificate for:
Patent No.: 4,525,341
Issued: Jun. 25, 1985
Appl. No.: 06/598,480
Filed: Apr. 9, 1984

(51) Int. Cl.
*A61K 9/00* (2006.01)
*A61K 31/07* (2006.01)
*A61K 31/365* (2006.01)
*A61K 31/59* (2006.01)

(52) U.S. Cl. ............ 424/43; 424/747; 514/52; 514/251; 514/356; 514/458; 514/474; 514/560; 514/563; 514/681; 514/725; 514/904

(58) Field of Classification Search ............. None
See application file for complete search history.

(56) References Cited

U.S. PATENT DOCUMENTS

| 3,282,781 A | 11/1966 | Macek et al. ............. 424/45 |
| 3,584,115 A | 6/1971 | Gebhart et al. ........... 424/45 |
| 3,957,966 A | 5/1976 | Valan ..................... 424/45 |
| 4,192,860 A | 3/1980 | Griffiths ................. 424/43 |
| 4,224,307 A | 9/1980 | Thiele et al. ............ 424/49 |
| 4,250,163 A | 2/1981 | Nagai et al. |

OTHER PUBLICATIONS

Physicians' Desk Reference, 36th Ed., pp. 545–546 "Norisodrine® Aerotrol®" 1982.*

* cited by examiner

*Primary Examiner*—Thurman K. Page

(57) ABSTRACT

A method for administering vitamins to an air-breathing animal consists of introducing the vitaminic aerosol containing a breath freshener into the nose or mouth opening of the animal.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claim 1 is cancelled.

\* \* \* \* \*